United States Patent [19]

Siuta et al.

[11] 4,185,033

[45] Jan. 22, 1980

[54] UREYLENE PHENYLENE ANIONIC NAPHTHALENESULFONIC ACIDS

[75] Inventors: Gerald J. Siuta, Yonkers; Ransom B. Conrow, Pearl River; John F. Poletto, Nanuet; Seymour Bernstein, New City, all of N.Y.

[73] Assignee: American Cyanamid Company, Stamford, Conn.

[21] Appl. No.: 923,745

[22] Filed: Jul. 11, 1978

[51] Int. Cl.$^2$ .................. C07C 143/30; A61K 31/185
[52] U.S. Cl. ............................... 260/506; 260/507 R; 424/315
[58] Field of Search ........................................ 260/506

[56] References Cited

U.S. PATENT DOCUMENTS 4,120,891  10/1978  Poletto et al. .................. 260/506

OTHER PUBLICATIONS

Adams et al., J. Chem. Soc., pp. 3739–3744 (1956).

*Primary Examiner*—Nicky Chan
*Attorney, Agent, or Firm*—Claude J. Caroli

[57] ABSTRACT

Novel ureylenebis-[substituted-phenylenecarbonylimino-substituted-phenylenecarbonylimino-naphthalenetrisulfonic acid, alkali metal salts], useful as inhibitors of the complement system of warm-blooded animals, the amino-substituted phenylenecarbonylimino, substituted-phenylenecarbonylimino-naphthalenetrisulfonic acid, alkali metal salts, which are new intermediates for the preparation of the active ureylenes, and the process for their preparation.

11 Claims, No Drawings

UREYLENE PHENYLENE ANIONIC NAPHTHALENESULFONIC ACIDS

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–66; J. Allergy Clin. Immunol., 53, 298–302 (1974); Cold Spring Harbor Conf. Cell Proliferation 2/Proteases Biol. Control/229–241 (1975); Ann. Review of Biochemistry, 44, 697 (1975); Complement in Clinical Medicine, Disease-a-month, (1975); Complement, Scope, December 1975; Annals of Internal Medicine, 84, 580–593 (1976); "Complement: Mechanisms and Functions", Prentice-Hall, Englewood Cliffs, N.J. (1976); Essays Med. Biochem., 2, 1–35 (1976); Hospital Practice, 12, 33–43 (1977); Perturbation of Complement in Disease, Chap. 15 in Biological Amplification Systems in Immunology (Ed. Day and Good), Plenum, New York and London (1977); Am. J. Clin. Pathology, 68, 647–659 (1977).

The complement system can be considered to consist of three sub-systems: (1) a recognition unit (C1$q$) which enables it to combine with antibody molecules that have detected a foreign invader; (2) an activation unit (C1$r$, C1$s$, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1–8, 1195, 1358–1364, 1482 (1977).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327–339 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 104, 279–288 (1970); The Journal of Immunology, 106, 241–245 (1971); The Journal of Immunology, 111, 1061–1066 (1973); Biochim. Biophys. Acta, 317, 539–548 (1973); Life Sciences, 13, 351–362 (1973); Journal of Immunology, 113, 584 (1974); Immunology, 26, 819–829 (1974); Journal of Medicinal Chemistry, 17, 1160–1167 (1974); Biochim. Biophys. Res. Comm., 67, 225–263 (1975); Ann. N. Y. Acad. Sci., 256, 441–450 (1975); Journal of Medicinal Chemistry, 19, 634–639, 1079 (1976); Journal of Immunology, 118, 466 (1977); Arch. Int. Pharmacodyn., 226, 281–285 (1977); Biochem. Pharmacol. 26, 325–329 (1977); Journal Pharm. Sci., 66, 1367–1377 (1977); Chem. Pharm. Bull., 25, 1202–1208 (1977); Biochim. Biophys. Acta, 484, 417–422 (1977) and Journal Clin. Microbiology, 5, 278–284 (1977).

It has been reported that the known complement inhibitors epsilon-amiocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808-812 (1972), 287, 452-454 (1972); Ann. Intern. Med., 84, 580-593 (1976); J. Allergy and Clin. Immunology, 60, 38-40 (1977).

It has also been reported that the drug pentosanpolysulfoester has an anticomplementary activity on human serum, both in vitro and in vivo, as judged by the reduction in total hemolytic complement activity; Pathologie Biologie, 25, 33-36, 25 (2), 105-108, 25 (3), 179-184 (1977).

It is known that the compound Suramin is moderately active as a complement inhibitor, and possesses the structure:

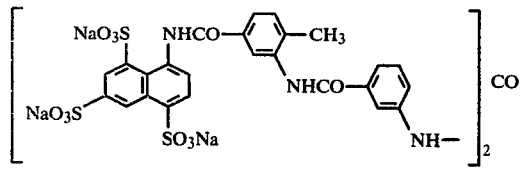

It now has been discovered that certain modifications of this structure provide compounds with enhanced inhibitory activity. This invention is based on such modifications.

The following publications, pertaining to the chemistry of Suramin, are related to the preparation of the novel compounds of this invention:

Bayer & Co., D.R.P. 278,122, June 22, 1913 [C.A. 9, 1096(1915)]
Bayer & Co., D.R.P. 288,272, Jan. 23, 1914 [C.A. 10, 2279(1916)]
Bayer & Co., D.R.P. 288,273, Feb. 21, 1914 [C.A. 10, 2279(1916)]
Frdl. 12, 185-186, 191-195 (1914-1916)
Danish Pat. No. 20,743 (1915)
Austrian Pat. No. 72,298 (1916)
Austrian Pat. No. 72,303 (1916)
U.S. Pat. No. 1,218,654 (1917)
U.S. Pat. No. 1,218,655 (1917)
Austrian Pat. No. 73,381 (1917)
U.S. Pat. No. 1,308,071 (1919)
E. Fourneau, J. Tréfouel, Mme. J. Tréfouel and J. Vallee, Acad. Sci. Comp. Rend., 178, 675-676 (1924)
E. Fourneau, F. Tréfouel and J. Vallee, Ann. de L'Institut Pasteur, 38 (2), 81-114 (1924)
B. Heymann, Zeitschrift Ang. Chem., 37, 585-589 (1924)
British Pat. No. 224,849 (1925)
U.S. Pat. No. 1,606,624 (1926)
J. E. R. McDonagh, Brit. Med. J., 693-696 (1926) [Chem. Zentralblatt, 1769-1770 (1926 II)]
W. Roehl, Arch. Schiff. Trop. Hyg., 30 (1), 103-111 (1926)
Poulenc Fréres, D.R.P. 427,857, Apr. 20, 1926 [Frdl. 15, 1434-1436 (1928)]
I. E. Balaban and H. King, J. Chem. Soc., 3068-3097 (1927)
H. Bauer and J. Becker, Arb. Staatsinst. Exptl. Therap., 16 pp. (1928)
U.S. Pat. No. 1,968,820 (1934)
O. Yu. Magidson, O. S. Madaeva and M. V. Rubtzov, Khim. Farm. Prom., 2, 89-94 L (1935) [C.A., 30, 4492 (1936)]
U.S. Pat. No. 2,126,180 (1938)
P. Pratsi and L. Raffa, Farmaco Sci e Tec (Pavia), 1, 21-34 (1946)
A. Spinks, Biochem. J., 42, 109-116 (1948)
E. D. Wills and A. Wormall, Biochem. J., 47, 158-170 (1950)
German Pat. No. 890,952 (1953) [C. A. 52, 14693 (1958)]
A. Adams, J. N. Ashley and H. Bader, J. Chem. Soc., 3739-3744 (1956) [C. A. 51, 4375i]

Publications related to the biological use of Sumarin compounds for the purpose of inhibiting the complement system, including humans, as determined by the in vivo and in vitro testing of the blood serum of warm-blooded animals are:

B. Stuber and K. Lang, Arch. Exptl. Path. Pharmacol., 154, 41-49 (1930) [C. A. 25, 3067(1931)]
F. Klopstock, Zeitschrift für Immunitatsforschung und experimentalle Therapie, 75, 348-354 (1932)
H. J. Schmid, Schweiz. Med. Woch., 96, 1267-1269 (1966)
K. Lauenstein, Bayer-Symposium I, 25-30 (1969)
J. S. C. Fong and R. A. Good, Clin. Exp. Immunol., 10, 127-138 (1972)
V. Eisen and C. Loveday, Br. J. Pharmac., 49, 678-687 (1973)
D. Brackertz and F. Keuppers, Allergol. Et Immunopath., 11, 163-168 (1974)
E. Raepple, H-U. Hill and M. Loos, Immunochemistry, 13 (3), 251-255 (1976)

SUMMARY OF THE INVENTION

This invention is concerned with ureylenebis[substituted-phenylenecarbonylimino-substituted-phenylenecarbonylimino]naphthalenetrisulfonic acids and all pharmaceutically acceptable salts thereof, having complement inhibiting activity, which are new compounds of the general formulae:

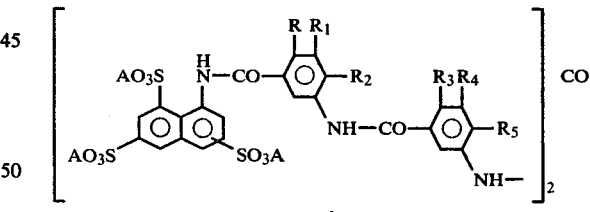

and

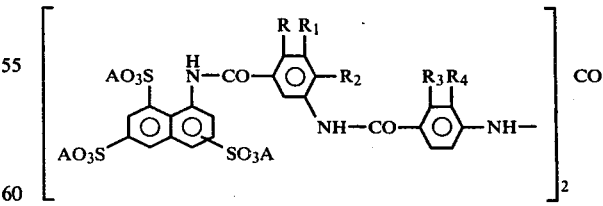

wherein R and $R_2$ are selected from the group consisting of hydrogen and methyl; $R_1$ and $R_4$ are selected from the group consisting of hydrogen and —COOB, wherein B is selected from the group consisting of hydrogen and a pharmaceutically acceptable salt cation; $R_3$ is selected from the group consisting of hydrogen and —$SO_3A$, wherein A is a pharmaceutically acceptable salt cation; $R_5$ is selected from the group consisting of hydrogen and methyl; with the proviso that $R_1$, $R_3$ and $R_4$ may not all be hydrogen; with the second proviso that $R_2$ and $R_5$ may not both be hydrogen; with the third proviso that neither phenyl moiety can contain both —$SO_3A$ and —COOB.

A preferred embodiment of this invention consists of those compounds wherein either $R_1$ or $R_4$, or both, are —COOB; and $R_3$ is hydrogen.

Another preferred embodiment of this invention consists of those compounds wherein $R_3$ is —$SO_3A$; and $R_1$ and $R_4$ are hydrogen.

This invention is also concerned with compounds of the formulae:

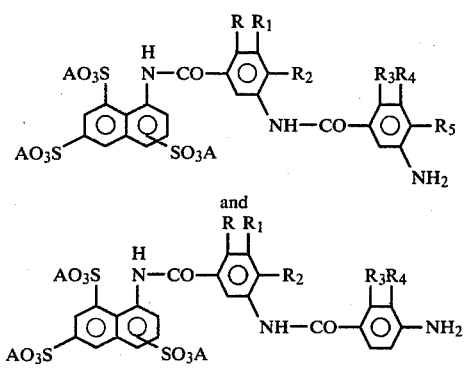

wherein R and $R_2$ are selected from the group consisting of hydrogen and methyl; $R_1$ and $R_4$ are selected from the group consisting of hydrogen and —COOB, wherein B is selected from the group consisting of hydrogen and a pharmaceutically acceptable salt cation; $R_3$ is selected from the group consisting of hydrogen and —$SO_3A$, wherein A is a pharmaceutically acceptable salt cation; $R_5$ is selected from the group consisting of hydrogen and methyl; with the proviso that $R_1$, $R_3$ and $R_4$ may not all be hydrogen; with the second proviso that $R_2$ and $R_5$ may not both be hydrogen; with the third proviso that neither phenyl moiety can contain boty —$SO_3A$ and —COOB; said compounds being useful as intermediates for the preparation of the complement inhibiting compounds described above. Some of the intermediate compounds also possess complement inhibiting activity.

DESCRIPTION OF THE INVENTION

The novel intermediate amine compounds of the invention are prepared by reacting the appropriate 8-amino-1,3,5-(and 1,3,6)-naphthalenetrisulfonic acid, trialkali metal salt with a nitrobenzoyl chloride such as m-nitrobenzoyl chloride and 3-nitro-p-toluoyl chloride, for 1.5–36 hours in an aqueous solution made alkaline with alkali meatl hydroxide, anhydrous alkali metal carbonate or alkali metal acetate trihydrate. After neutralization, the solution is diluted with absolute ethanol to provide the corresponding nitro-substituted-phenylenecarbonylimino-1,3,5(and 1,3,6)-naphthalenetrisulfonic acid, trialkali metal salt.

Hydrogenation of the preceding nitro compound trialkali metal salts using 10% palladium-carbon catalyst, filtration, concentration and treatment with absolute ethanol provides the corresponding amino-substituted-phenylenecarbonylimino-naphthalenetrisulfonic acid, trialkali metal salt compounds.

The amino compounds above, dissolved in aqueous media and made alkaline with either alkali metal hydroxide or anhydrous alkali metal carbonate are reacted once more with the desired substituted nitrobenzoyl chloride listed above for 1.5–36 hours. After neutralization, the solution is diluted with absolute ethanol to provide the corresponding nitro-substituted-phenylenecarbonylimino-substituted-phenylenecarbonylimino-naphthalenetrisulfonic acid, trialkali metal salt.

The novel intermediate amine compounds of the invention are then obtained by hydrogenation of the above nitro compounds using 10% palladium-carbon catalyst in water as previously described, filtration and evaporation of the filtrate produces a residue which is dissolved in water and precipitated with absolute ethanol to provide the desired product.

The novel ureylene compounds of the invention, which are active complement inhibitors, are then provided by treatment of the above intermediate amine compounds with phosgene in aqueous media made alkaline with alkali metal carbonate or pyridine, neutralization and precipitation from aqueous solution with alcohol.

This invention is concerned with a method of inhibiting the complement system in a body fluid, such as blood serum, which comprises subjecting body fluid complement to the action of an effective complement inhibiting amount of a compound encompassed within the formulae hereinabove. The method of use aspect of this invention is also concerned with a method of inhibiting the complement system in a warm-blooded animal which comprises administering to said animal an effective complement inhibiting amount of a compound encompassed within the formulae hereinabove. Body fluid can include blood, plasma, serum, synovial fluid, cerebrospinal fluid, or pathological accumulations of fluid such as pleural effusion, etc.

Compounds of the present invention find utility as complement inhibitors in body fluids and as such may be used to ameliorate or prevent those pathological reactions requirin the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary antioneurotic edema (treated with Suramin, etc.) and inflammatory states induced by the action of bacterial or lysosomal enzymes on the appropriate complement components as for example, inflammation following coronary occulusion. They may also be useful in the treatment of transparent rejection and as blood culture or transport mediums.

The compounds of the present invention may be administered internally, e.g., orally or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to about is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests code 026, 035, 036, Cap 50, % inhibition and Forssman shock. Table I shows that the compounds of the invention possess highly significant in vitro and in vivo complement inhibiting activity in warm-blooded animals and are more active than the reference compound Suramin. Results obtained are listed in Table I.

Table II shows the complement inhibiting activity of the intermediate compounds of the invention.

TABLE I

| | Biological Activities | | | | In Vivo Activity (Guinea Pig) % Inhibition Intraperitoneal Time (Minutes) | | |
|---|---|---|---|---|---|---|---|
| Compound | Cl 026* Wells | C-Late 035* Wells | Shunt Inhibition 036* Wells | Cap 50* | 30 | 60 | 120 |
| Suramin | +4** | +2** | — | 361 | −9 | −17 | −44 |
| 5,5''-Ureylenebis[2'-methyl-5'-(4,6,8-trisulfo-1-naphthyl) carbamoyl)-isophthalanilic acid], octasodium salt | +5 | +2 | +2** | 249 | −17 | −50 | −57 |
| 5,5''-Ureylenebis[2'-methyl-5'-(4,6,8-trisulfo-1-naphthylcarbamoyl]-isophthalanilic acid],hexasodium salt | +5 | +2 | +2 | 295 | | | |
| 5,5'-Ureylenebis[(4-methyl-3,1-phenylenecarbonyl)imino] bis[N-(4,6,8-trisulfo-1-naphthyl)isophthalamic acid], hexasodium salt | +5 | +2 | +1 | 47 | | | |
| 5,5'-[Ureylenebis[(4-methyl-3,1-phenylenecarbonylimino]] bis[N-(4,6,8-trisulfo-1-naphthyl)isophthalamic acid, octasodium salt | +5 | — | — | | | | |
| 8,8'-[Ureylenebis[(2-sulfo-4,1-phenylenecarbonyl)imino-(4-methyl-3,1-phenylenecarbonylimino]]di-1,3,5-naphthalenetrisulfonic acid, octasodium salt | +3 | +1 | +2 | 187 | | | |

*Code designation for tests employed as referred herein.
**Activity in wells a serial dilution assay. Higher well number indicates higher activity. The serial dilutions are two-fold.

TABLE II

| | (INTERMEDIATES) Biological Activities | | | |
|---|---|---|---|---|
| Compound | Cl 026* Wells | C-Late 035* Wells | Shunt Inhibition 036* Wells | Cap 50* |
| 5-Amino-2'-methyl-5'(4,6,8-trisulfo-1-naphthyl)carbamoyl)isophthalanilic acid, trisodium salt | +2** | N | N | |
| 5-(3-Amino-p-toluamido)-N-(4,6,8-trisulfo-1-naphthyl)isophthalamic acid, trisodium salt | +3 | N | N | >500 |
| 8-[3-(4-Amino-2-sulfobenzamido)-p-toluamido]-1,3,5-naphthalenetrisulfonic acid, tetrasodium salt | +2 | N | N | |

*Code designation for tests employed as referred herein.
**Activity in wells a serial dilution assay. Higher well number indicates higher activity. The serial dilutions are two-fold.
N = Negative (no activity).

DETAILED DESCRIPTION OF THE INVENTION

EXAMPLE 1

5-Amino-2'-methyl-5'-(4,5,8-trisulfo-1-naphthylcarbamoyl) isophthalanilic acid, trisodium salt To a warm solution of 106.4 g of (80.5%) 8-amino-1,3,5-naphthalenetrisulfonic acid in 100 ml of water and 45.0 ml of 5 N sodium hydroxide is slowly added 500 ml of absolute ethanol with vigorous stirring for 30 minutes. The mixture is cooled to room temperature and filtered. The precipitate is washed with 80% aqueous ethanol, ethanol and ether and is dried in vacuo at 110° C. for 16 hours to give 103.7 g of 8-amino-1,3,5-naphthalenetrisulfonic acid trisodium salt.

A mixture of 25.0 g of 4-methyl-3-nitrobenzoic acid and 50 ml of thionyl chloride is refluxed for 3½ hours in a 110° C. oil bath. The resulting solution is evaporated in vacuo to an oil. The oil is distilled at a pressure of 0.5 mm of mercury and an oil bath temperature of 145°–160° C. The fraction, bp 108°–113° C., is collected to give 24.3 g of 3-nitro-p-toluoyl chloride.

To a stirred solution of 22.5 g of 8-amino-1,3,5-naphthalenetrisulfonic acid trisodium salt in 160 ml of water is added 11.0 g of the preceding product with a small amount of ether. Stirring is continued, and after one hour 1.0 g of sodium acetate trihydrate and 1.0 g of 3-nitro-p-toluoyl chloride are added. The mixture is stirred an additional 3 hours and the above addition of sodium acetate and 3-nitro-p-toluoyl chloride is repeated. The mixture is stirred an additional hour, acidified to Congo red indicator paper with hydrochloric acid and filtered. The filtrate is neutralized with sodium hydroxide, concentrated, dissolved in 50 ml of water and added to one liter of ethanol with stirring for 16 hours. The solid is filtered and forms a gel on washing with ethanol. The gel is dissolved in water and evaporated. The residue is dissolved in 35 ml of hot water and 320 ml of absolute ethanol is added with stirring. The mixture solidifies and water is added to allow filtration. The solid is washed with ether and dried in vacuo. The filtrate is treated by stirring with one liter of ethanol, the separated solid is collected, washed with ether, and dried to yield a combined total of 23.9 g of 8-(3-nitro-p-toluamido)-1,3,5-naphthalenetrisulfonic acid trisodium salt.

A 22.0 g portion of the preceding product, 200 ml of water and 2.5 g of 10% palladium-on-carbon catalyst is hydrogenated in a Parr shaker until no additional hydrogen is absorbed. The resulting mixture is filtered through diatomaceous earth, the residue is washed with water, and the filtrate is evaporated. The residue is dissolved in 50 ml of water and added to 900 ml of absolute ethanol. The mixture is warmed on a steam bath, then is stirred at room temperature for 3 hours. The mixture is filtered and the solid is washed with ethanol, then ether and dried in vacuo to give 16.89 g of 8-(3-amino-p-toluamido)-1,3,5-naphthalenetrisulfonic acid trisodium salt.

A mixture of 60.0 g of 5-nitroisophthalic acid, 300 ml of thionyl chloride and one ml of dimethylformamide is stirred at room temperature for 30 minutes, then is refluxed for one hour. The resulting clear solution is allowed to stand 24 hours, then is evaporated to a small volume in vacuo. The evaporation step is repeated with toluene and the resulting liquid is diluted with 250 ml of hexane. The mixture is stirred and cooled until the resulting oil is solidified. The product is ground to a powder and is recrystallized twice from carbon tetrachloride to give 47.4 g of 5-nitroisophthaloyl chloride.

A solution of 2.78 g of 5-nitroisophthaloyl chloride in 50 ml of ether is added to a stirred mixture of 6.5 g of 8-(3-amino-p-toluamido)-1,3,5-naphthalenetrisulfonic acid, trisodium salt, 3.2 g of sodium acetate trihydrate, 50 ml of water and 40 ml of ether over a 40 minute period. The mixture is stirred for an additional 30 minutes, then is evaporated. The residue is dissolved in 20 ml of hot water, then is placed in an icebox overnight. The precipitate is collected, washed with ice-water, 80% aqueous ethanol, ethanol and ether and is dried to yield 2.9 g of 2′-methyl-5-nitro-5′-(4,6,8-trisulfo-1-naphthylcarbamoyl)isophthalanilic acid, trisodium salt.

A mixture of 4.21 g of the product prepared as described above, 120 ml of water and 0.70 g of 10% palladium-on-carbon catalyst is hydrogenated on a Parr shaker until no additional hydrogen is absorbed. The reaction mixture is filtered through diatomaceous earth and the filtrate is evaporated. The residue is dissolved in 20 ml of hot water and ethanol is added to a total volume of 250 ml with formation of a gel. The gel is separated, washed with ethanol and ether and dried to yield 3.25 g of the product of the Example.

EXAMPLE 2

5,5″-Ureylenebis[2′-methyl-5′-(4,6,8-trisulfo-1-naphthylcarbamoyl)isophthalanilic acid], octasodium salt A solution of 3.0 g of the product of Example 1, and 0.90 g of anhydrous sodium carbonate in 30 ml of water is phosgenated until it is acidic to Congo Red indicator paper.

The pH of the solution is adjusted to 7.0 with anhydrous sodium carbonate, the solution is filtered, and the filtrate is evaporated. The residue is dissolved in 20 ml of hot water, then 80 ml of absolute ethanol is added with formation of a gum. The supernatant is decanted and set aside for Example 3. The gum is triturated with ethanol to provide a solid. The solid is stirred for 2 hours in ethanol and is collected. The solid is washed with ethanol and ether and is dried to yield 2.0 g of the product of the Example.

EXAMPLE 3

5,5″-Ureylenebis[2′-methyl-5′-(4,6,8-trisulfo-1-naphthylcarbamoyl)isophthalanilic acid], hexasodium salt The decanted supernatant set aside in Example 2 separates a solid on standing. The solid is collected and washed with ethanol and ether. The solid is dissolved in 2.0 ml of water and is acidified with hydrochloric acid, then 8.0 ml of absolute ethanol is added with formation of a precipitate. The product is collected, washed with ethanol and ether and dried to give 175 mg of the product of the Example.

EXAMPLE 4

5-(3-Amino-p-toluamido)-N-(4,6,8-trisulfo-1-naphthyl)isophthalamic acid, trisodium salt A 35.0 g portion of 5-nitroiosphthaloyl chloride is added to 600 ml of methanol with stirring producing a precipitate. The mixture is heated to solution, then is chilled, filtered and dried to yield 31.75 g of dimethyl 5-nitroisophthalate.

A mixture of 7.46 g of potassium hydroxide in 87.5 ml of methanol is added to a stirred solution of 31.75 g of the preceding product in 331.0 ml of acetone. A solid is precipitated and stirring is continued for 16 hours. The solid (A) is filtered off, washed with ether and set aside. The filtrate is evaporated, the residue is extracted with 125 ml of warm water and is filtered. The filtrate is acidified with dilute hydrochloric acid to produce a precipitate which is collected and dried to yield 3.4 g of product. The solid (A) above is extracted with 250 ml of warm water and is filtered. The filtrate is filtered again at room temperature, acidified with dilute hydrochloric acid and cooled. The precipitate is collected and dried to give 18.25 g of additional product identified as 5-nitro-isophthalic acid, 3-methyl ester.

A mixture of 18.38 g of the above product, 60 ml of thionyl chloride and 0.37 ml of dimethylformamide is heated at 60° C. for 2.5 hours. The solution is evaporated, then is treated with toluene, and again is evaporated. The residue is slurried in hot diethyl ether and the ether volume is reduced by evaporation. The mixture is chilled and filtered. The precipitate is washed with cold ether and is dried. The material is extracted with 500 ml of boiling hexane by decantation. The hexane is cooled and filtered to yield 14.1 g of 3-carbomethoxy-5-nitrobenzoyl chloride.

To a solution of 14.0 g of 8-amino-1,3,5-naphthalenetrisulfonic acid trisodium salt and 8.96 g of sodium acetate trihydrate in 150 ml of water is added with stirring 8.0 g of 3-carbomethoxy-5-nitrobenzoyl chloride. Stirring is continued for 2 hours then 18.0 ml of diethyl ether is added and stirring is continued for one additional hour. An additional 1.12 g of sodium acetate is added along with 1.0 g of 3-carbomethoxy-5-nitrobenzoyl chloride with continued stirring for one hour. The mixture is filtered and the filtrate is concentrated. The residue is dissolved in 100 ml of hot water, then 100 ml of absolute ethanol is added with formation, on standing, of a precipitate. The material is filtered, washed with 80% aqueous ethanol, ethanol and ether and dried to yield 17.35 g of 5-nitro-N-4,6,8-trisulfo-1-naphthylisophthalamic acid methyl ester, trisodium salt.

A 3.27 g portion of the preceding product and 700 mg of 10% palladium-on-carbon catalyst in 100 ml of water is hydrogenated in a Parr shaker until no more hydrogen is absorbed. The resulting mixture is filtered through diatomaceous earth and the filtrate is concentrated. The residue is dissolved in about 15 ml of hot water and absolute ethanol is added to a total volume of 250 ml with formation of a precipitate. The precipitate is collected by filtration, washed with ethanol and ether and dried to yield 2.4 g of 5-amino-N-4,6,8-trisulfo-1-naphthylisophthalamic acid methyl ester, trisodium salt.

A mixture of 25.0 g of 4-methyl-3-nitrobenzoic acid and 50 ml of thionyl chloride is refluxed for 3.5 hours in a 110° C. oil bath. The resulting solution is evaporated in vacuo to an oil. The oil is distilled at a pressure of 0.5 mm of mercury and an oil bath temperature of 145°–160° C. The fraction, bp 108°–113° C., is collected to give 24.3 g of 3-nitro-p-toluoyl chloride.

To a stirred solution of 1.6 g of 5-amino-N-4,6,8-trisulfo-1-naphthylisophthalamic acid methyl ester, trisodium salt, 15.0 ml of water and 270 mg of sodium carbonate is added 611 mg of the preceding compound. The reaction mixture is stirred at room temperature for 3 hours, then is acidified with dilute hydrochloric acid and poured into absolute ethanol. The resulting precipitate is collected, washed with ethanol and ether and dried to yield 1.59 g of 5-(3-nitro-p-toluamido)-N-(4,6,8-trisulfo-1-naphthyl)isophthalamic acid methyl ester, trisodium salt.

A 1.39 g portion of the product above is dissolved by stirring in 50 ml of 1 N sodium hydroxide. Stirring is continued for 3.5 hours, then the solution is acidified with dilute hydrochloric acid affording a white gelatinous material. Ethanol is then added and the mixture is evaporated. The residue is dissolved in hot water, it triturated with ethanol and cooled. The precipitate is collected and washed twice with both ethanol and ether and is dried to yield 460 mg of 5-(3-nitro-p-toluamido)-N-(4,6,8-trisulfo-1-naphthyl)isophthalamic acid, trisodium salt.

A mixture of 300 mg of the product above, 50.0 ml of water and 30.0 mg of 10% palladium-on-carbon catalyst is hydrogenated at room temperature for 3 hours. The resulting mixture is filtered through diatomaceous earth and the filtrate is evaporated. The residue is reprecipitated from water and ethanol and is collected and dried to yield 255 mg of the product of the Example.

EXAMPLE 5

5,5′-[Ureylenebis[(4-methyl-3,1-phenylenecarbonyl)imino]]bis[N-(4,6,8-trisulfo-1-naphthyl)isophthalamic acid], octasodium salt A solution of 240 mg of the product of Example 4, 10 ml of water and 27 mg of anhydrous sodium carbonate is phosgenated until acidic to Congo Red indicator paper, then an additional 77 mg of sodium carbonate is added and phosgene is bubbled in until acidic again. The solution is neutralized with sodium carbonate and the reaction mixture is evaporated, the residue is dissolved in hot water and ethanol is added until a precipitate forms. The mixture is cooled and the precipitate is collected. The solid is washed twice with both ethanol and ether and dried to yield 199 mg of the product of the Example.

EXAMPLE 6

5,5′-Ureylenebis[(4-methyl-3,1-phenylenecarbonyl)-imino]bis[N-(4,6,8-trisulfo-naphthyl)isophthalamic acid], hexasodium salt A solution of 100 mg of the product of Example 5 in 10 ml of water is acidified with glacial acetic acid. The mixture is evaporated and the residue is dissolved in hot water. Ethanol is added until a precipitate forms. The mixture is cooled and the precipitate is collected. The solid is washed twice with both ethanol and ether and is dried to yield 85.0 mg of the product of the Example.

EXAMPLE 7

8-[3-(4-Amino-2-sulfobnzamido)-p-toluamido]-1,3,5-naphthalenetrisulfonic acid tetrasodium salt To a stirred solution of 6.5 g of 8(3-amino-p-toluamido)-1,3,5-naphthalenetrisulfonic acid, trisodium salt (prepared in Example 1) and 2.4 g of sodium acetate trihydrate in 43.0 ml of water is added 3.07 g of 4-nitro-2-sulfobenzoic acid anhydride. The mixture is stirred for 30 minutes then is filtered. The filtrate is acidified with 0.98 ml of concentrated hydrochloric acid and evaporated in vacuo. The residue is dissolved in 20 ml of hot water which is added to 130 ml of absolute ethanol forming a gelatinous precipitate. The material is collected and washed with 80% aqueous ethanol, ethanol and ether and is dried to yield 4.2 g of 8-[3-(4-nitro-2-sulfobenzamido)-p-toluamido]-1,3,5-naphthalenetrisulfonic acid, tetrasodium salt.

A mixture of 5.95 g of the preceding product, 100 ml of water and 0.80 g of 10% palladium-on-carbon catalyst is hydrogenated as described in Example 1. The resulting mixture is filtered through diatomaceous earth and the filtrate is evaporated. The residue is dissolved in 20 ml of hot water and added to 230 ml of absolute ethanol separating an oil. The supernatant is decanted and evaporated. The residue is dissolved in 10 ml of water and 230 ml of absolute ethanol is added forming a fine precipitate. The precipitate is collected, washed with ethanol and ether and dried to yield 2.95 g of the product of the Example.

EXAMPLE 8

8,8'-[Ureylenebis[(2-sulfo-4,1-phenylenecarbonyl)imino(4-methyl-3,1-phenylenecarbonyl)imino]]-di-1,3,5-naphthalenetrisulfonic acid, octasodium salt A cooled solution of 4.0 g of the product of Example 7 and 1.07 g of anhydrous sodium carbonate in 30.0 ml of water is phosgenated until acidic to Congo Red indicator paper. The pH of the solution is adjusted to 8.0 with sodium carbonate, then to pH 6.5 with glacial acetic acid. The solution is filtered and the filtrate is evaporated. The residue is dissolved in 25.0 ml of hot water, then 50 ml of absolute ethanol is added with stirring, resulting in precipitation of a product. The material is collected by filtration, washed with 80% aqueous ethanol, ethanol and ether and is dried to yield 3.0 g of the product of the Example.

EXAMPLE 9

5-Amino-2'-methyl-5'-(3,6,8-trisulfo-1-naphthylcarbamoyl)isophthalanilic acid, trisodium salt Following the procedure of Example 1, employing 8-amino-1,3,6-naphthalenetrisulfonic acid, trisodium salt provides the product of the Example.

EXAMPLE 10

5,5''-Ureylenebis[2'-methyl-5'-(3,6,8-trisulfo-1-naphthylcarbamoyl)isophthalanilic acid], octasodium salt Following the procedure of Example 2, phosgenation of the product of Example 9 provides the product of the Example.

EXAMPLE 11

5-(3-Amino-p-toluamido)-N-(3,6,8-trisulfo-1-naphthyl)isophthalamic acid, trisodium salt Following the procedure of Example 4, employing 8-amino-1,3,6-naphthalenetrisulfonic acid, trisodium salt provides the product of the Example.

EXAMPLE 12

5,5'-[Ureylenebis[(4-methyl-3,1-phenylenecarbonyl)imino]]-bis[N-(3,6,8-trisulfo-1-naphthyl)isophthalamic acid], octasodium salt Following the procedure of Example 5, phosgenation of the product of Example 11 provides the ureylene of the Example.

EXAMPLE 13

8-[3-(4-Amino-2-sulfobenzamido)-p-toluamido]-1,3,6-naphthalenetrisulfonic acid, tetrasodium salt Following the procedure of Example 7, employing 8-(3-amino-p-toluamido)-1,3,6-naphthalenetrisulfonic acid, trisodium salt gives the product of the Example.

EXAMPLE 14

8,8'-[Ureylenebis[(2-sulfo-4,1-phenylenecarbonyl)imino(4-methyl-3,1-phenylenecarbonyl)imino]]-di-1,3,6-naphthalenetrisulfonic acid, octasodium salt Following the procedure of Example 8, phosgenation of the product of Example 13 provides the ureylene of the Example.

EXAMPLE 15

| Preparation of Compressed Tablet | |
|---|---|
| Ingredient | mg/Tablet |
| Active Compound | 0.5-500 |
| Dibasic Calcium Phosphage N.F. | qs |
| Starch USP | 40 |
| Modified Starch | 10 |
| Magnesium Stearate USP | 1-5 |

EXAMPLE 16

| Preparation of Compressed Tablet - Sustained Action | |
|---|---|
| Ingredient | mg/Tablet |
| Active Compound as Aluminum Lake*, Micronized | 0.5-500 (as acid equivalent) |
| Dibasic Calcium Phosphate N.F. | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 17

| Preparation of Hard Shell Capsule | |
|---|---|
| Ingredient | mg/Capsule |
| Active Compound | 0.5-500 |
| Lactose, Spray Dried | qs |
| Magnesium Stearate | 1-10 |

EXAMPLE 18

| Preparation of Oral Liquid (Syrup) | |
|---|---|
| Ingredient | % W/V |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 19

| Preparation of Oral Liquid (Elixir) | |
|---|---|
| Ingredient | % W/V |
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 20

| Preparation of Oral Suspension (Syrup) | |
|---|---|
| Ingredient | % W/V |
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |

-continued

Preparation of Oral Suspension (Syrup)

| Ingredient | % W/V |
|---|---|
| Methyl Paraben USP | 0.18 |
| Propyl Paragen USP | 0.02 |
| Liquid Sugar | 75.0 |
| Purified Water qs ad | 100.0 |

EXAMPLE 21

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 22

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 23

Preparation of Intra-Articular Product

| Ingredient | Amount |
|---|---|
| Active Compound | 2–20 mg |
| NaCl (physiological sadine) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 24

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 25

Preparation of Dental Paste

| Ingredient | % W/V |
|---|---|
| Active Compound | 0.05–5 |
| Zinc Oxide | 15 |
| Polyethylene Glycol 4000 USP | 50 |
| Distilled Water qs | 100 |

EXAMPLE 26

Preparation of Dental Ointment

| Ingredient | % W/V |
|---|---|
| Active Compound | 0.05–5 |
| Petrolatum, White USP qs | 100 |

EXAMPLE 27

Preparation of Dental Cream

| Ingredient | % W/V |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methylparaben USP | 0.18 |
| Propyl Paraben USP | 0.02 |
| Distilled Water qs | 100 |

EXAMPLE 28

Preparation of Topical Cream

| Ingredient | % W/V |
|---|---|
| Active Compound | 0.05–5 |
| Sodium Laurylsulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 29

Preparation of Topical Ointment

| Ingredient | % W/V |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 30

Preparation of Spray Lotion (non-Aerosol)

| Ingredient | % W/V |
|---|---|
| Active Compound | 0.05–5 |
| Isopropyl Myristate | 20 |
| Alcohol (Denatured) qs | 100 |

EXAMPLE 31

Preparation of Buccal Tablet

| Ingredient | g/Tablet |
|---|---|
| Active Ingredient | 0.00325 |
| 6 x Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |

| Preparation of Buccal Tablet -continued | |
|---|---|
| Ingredient | g/Tablet |
| | 0.32500 |

The final tablet will weigh about 325 mg. and may be compressed into buccal tablets in flat faced or any other tooling shape convenient for buccal administration.

EXAMPLE 30

| Preparation of Lozenge | |
|---|---|
| Ingredient | g/Lozenge |
| Active Ingredient | 0.0140 |
| Kompact ® Sugar (Sucrest Co.) | 0.7138 |
| 6 x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into 5/8" flat based lozenge tooling. Other shapes may also be utilized.

We claim:

1. A compound of the formulae:

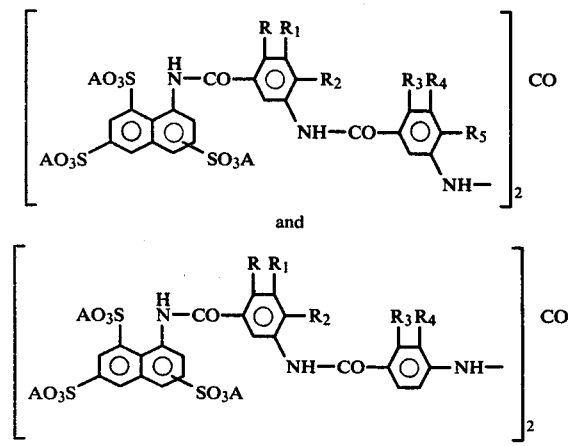

and wherein R and $R_2$ are selected from the group consisting of hydrogen and methyl; $R_1$ and $R_4$ are selected from the group consisting of hydrogen and —COOB, wherein B is selected from the group consisting of hydrogen and a pharmaceutically acceptable salt cation; $R_3$ is selected from the group consisting of hydrogen and —$SO_3A$, wherein A is a pharmaceutically acceptable salt cation; $R_5$ is selected from the group consisting of hydrogen and methyl; with the proviso that $R_1$, $R_3$ and $R_4$ may not all be hydrogen; with the second proviso that $R_2$ and $R_5$ may not both be hydrogen and when $R_5$ is not present, $R_2$ must be methyl; and with the third proviso that when $R_3$ is —$SO_3A$, $R_4$ may not be —COOB.

2. A compound according to claim 1, wherein either $R_1$ or $R_4$, or both, are —COOB; and $R_3$ is hydrogen.

3. A compound according to claim 1, wherein $R_3$ is —$SO_3A$; and $R_1$ and $R_4$ are hydrogen.

4. The compound according to claim 1, 5,5''-ureylenebis[2'-methyl-5'-(4,6,8-trisulfo-1-naphthylcarbamoyl)isophthalanilic acid], octasodium salt.

5. The compound according to claim 1, 5,5''-ureylenebis[2'-methyl-5'-(4,6,8-trisulfo-1-naphthylcarbamoyl)isophthalanilic acid], hexasodium salt.

6. The compound according to claim 1, 5,5'-[ureylenebis[(4-methyl-3,1-phenylenecarbonyl)imino]-bis[N-(4,6,8-trisulfo-1-naphthyl)-isophthalamic acid], octasodium salt.

7. The compound according to claim 1, 5,5'-ureylenebis[(4-methyl-3,1-phenylenecarbonyl)imino]-bis[N-(4,6,8-trisulfo-1-naphthyl)-isophthalamic acid], hexasodium salt.

8. The compound according to claim 1, 8,8'-[ureylenebis[(2-sulfo-4,1-phenylenecarbonyl)imino(4-methyl-3,1-phenylenecarbonyl)imino]]di-1,3,5-naphthalenetrisulfonic acid, octasodium salt.

9. The compound according to claim 1, 5,5''-ureylenebis[2'-methyl-5'-(3,6,8-trisulfo-1-naphthylcarbamoyl)isophthalanilic acid], octasodium salt.

10. The compound according to claim 1, 5,5'-[ureylenebis[(4-methyl-3,1-phenylenecarbonyl)imino]]-bis[N-(3,6,8-trisulfo-1-naphthyl)isophthalamic acid], octasodium salt.

11. The compound according to claim 1, 8,8'-[ureylenebis[(2-sulfo-4,1-phenylenecarbonyl)imino(4-methyl-3,1-phenylenecarbonyl)imino]]-di-1,3,6-naphthalenetrisulfonic acid, octasodium salt.

* * * * *